United States Patent
Kiso et al.

(10) Patent No.: US 7,001,611 B2
(45) Date of Patent: Feb. 21, 2006

(54) COMPOSITIONS NORMALIZING CIRCADIAN RHYTHM

(75) Inventors: Yoshinobu Kiso, Osaka (JP); Yoshiko Ono, Osaka (JP); Katsuya Nagai, Osaka (JP)

(73) Assignee: Suntory Limited, Osaka (JP)

( * ) Notice: Subject to any disclaimer, the term of this patent is extended or adjusted under 35 U.S.C. 154(b) by 0 days.

(21) Appl. No.: 10/030,715

(22) PCT Filed: May 15, 2001

(86) PCT No.: PCT/JP01/04027

§ 371 (c)(1),
(2), (4) Date: Jan. 14, 2002

(87) PCT Pub. No.: WO01/87291

PCT Pub. Date: Nov. 22, 2001

(65) Prior Publication Data

US 2003/0091614 A1    May 15, 2003

(30) Foreign Application Priority Data

May 6, 2000    (JP)    .............................. 2000-143039

(51) Int. Cl.
*A61K 47/00*    (2006.01)
*A61K 31/405*   (2006.01)
*A61K 31/12*    (2006.01)

(52) U.S. Cl. ...................... 424/439; 514/415; 514/691

(58) Field of Classification Search ................ 424/439; 514/691, 415
See application file for complete search history.

(56) References Cited

FOREIGN PATENT DOCUMENTS

| EP | 770385 | 5/1997 |
|---|---|---|
| JP | 2-49091 | 2/1990 |
| JP | 5-124958 | 5/1993 |
| JP | 7-300421 | 11/1995 |
| JP | 10-155459 | 6/1998 |

OTHER PUBLICATIONS

The Merck Manual, fifteenth addition, 1987, pp. 1375-1377.*
Stedman's Medical Dictionary 27th Edition, 2000, definition of "stress".*
O. Hayaishi, "Properties and Function of Indoleamine 2,3-Dioxygenase", J. Biochem, vol. 79, (1976), pp. 13-21.
J. Redman et al., "Free-Running Activity Rhythms in the Rat: Entrainment by Melatonin", Science, vol. 219 (Mar. 4, 1983), pp. 1089-1091.

* cited by examiner

*Primary Examiner*—Shengjun Wang
(74) *Attorney, Agent, or Firm*—Paul E. White, Jr.; Manelli Denison & Selter PLLC

(57) ABSTRACT

The present invention provides a circadian rhythm normalizing composition containing astaxanthin and/or its ester as an active ingredient, and a composition having the action of enhancing the circadian rhythm normalizing action of melatonin by protecting melatonin. The composition can be in the form of a drug, a functional food, a food or a beverage.

This composition has a circadian rhythm normalizing action, and has the action of preventing or alleviating sleep disorder and various diseases due to disturbance of the circadian rhythm.

3 Claims, 10 Drawing Sheets

COMPOSITIONS NORMALIZING CIRCADIAN RHYTHM

This application is the national phase of international application PCT/JP01/04027 filed 15 May 2001 which designated the U.S. which claims foreign priority of JP143039/2000, filed May 16, 2000.

TECHNICAL FIELD

This invention relates to a circadian rhythm normalizing composition containing astaxanthin and/or its ester as an active ingredient, and a composition having astaxanthin and/or its ester incorporated in or combined with melatonin in order to enhance the somniferous action of melatonin. The invention also relates to a composition incorporating astaxanthin and/or its ester in order to enhance the somniferous action of melatonin already present in vivo.

BACKGROUND ART

Living beings on the Earth have a mechanism, called a biological clock, for a circadian rhythm tuned to a 24-hour environmental cycle from the daytime to the nighttime, such as a light-dark cycle, occurring as the Earth revolves on its own axis. The biological clock is controlled by the hypothalamic suprachiasmatic nucleus of the brain. We have the circadian rhythm of sleep-wakefulness and eating behavior attributed to the biological clock.

The circadian rhythm is observed not only in sleep and diet, but also in most of the body temperature, blood pressure, heart beat, and internal secretion. Understanding the circadian rhythms of the autonomic nervous system, endocrine system, hemodynamics, etc and keeping them normal are considered important to the treatment and prevention of cardiovascular diseases. In modern society, artificial and irregular lives due to work shifts, long distance jet flights, aging of the society, diverse life styles, and so on are becoming routine. In this modern society, there are rapid increases in various diseases attributed to biorhythm disorders, including circadian rhythm-associated sleep disorder. Effective therapeutic action against such diseases is urgently needed. A patient with desynchronosis syndrome (time zone fatigue) due to disturbance of the circadian rhythm falls into insomnia at night, and suffers from a sleep attack during the daytime. The patient is also annoyed by headache, tinnitus, palpitation, nausea, abdominal pain, or diarrhea, and presents with symptoms of decline in judgment and decrease in concentration. Draw-back sleep phase syndrome (DSPS) shows the highest morbidity rate during puberty (Diagnostic Classification Steering Committee, Thorpy M. J.: International Classification of Sleep Disorders: Diagnostic and Coding Manual., American Sleep Disorders Association, Rochester. 1990). Such circadian rhythm-associated sleep disorder among young people makes social adaptation difficult, and hinders the patients from exhibiting their abilities (Kajimura et al.: The Japanese Journal of Clinical Medicine, Vol. 56, No. 2, p. 404, 1998).

Among methods for regulating the disturbance of the circadian rhythm producing such symptoms are psychotherapeutic approaches, non-pharmacotherapies, and pharmacotherapies. The non-pharmacotherapies include irradiation with high illuminance light, which nowadays is actively used for treatment of seasonal affective disorder and circadian rhythmical sleep disorder. For pharmacotherapies, vitamin $B_{12}$, benzodiazepine hypnotics, etc. are used, but they do not take effect without fail, and established pharmacotherapy is expected. Compared with the hitherto predominant barbiturate or non-barbiturate hypnotics, benzodiazepine hypnotics minimally cause drug tolerance or dependence, and have relatively high safety. However, the benzodiazepine hypnotics are known to produce adverse reactions, such as muscle relaxant action, carry-over effect, and amnestic action, and their use requires due care. That is, there are currently not any excellent compounds which are safe, effective and possessive of a circadian rhythm normalizing action.

Melatonin is expected as a new compound for regulating the circadian rhythm. Melatonin is a hormone mainly produced by the pineal body, and its production shows marked diurnal fluctuations. Its amount produced in the nighttime reaches as large as 50 to 100 times that during the daytime.

When the nocturnal secretion of melatonin is suppressed by the administration of a β-blocker, there occur sleep-wakefulness rhythm disorders, for example, a low quality sleep such as increased midway wakening at night (Brismar et al.: Acta. Med. Scand., 223, p. 525, 1988) and a decreased wakefulness level during the daytime (Dimenas et al.: J. Clin. Pharmacol., 30, s103, 1990). Behind sleep disorder in elderly people lies a decrease in melatonin secretion, and melatonin replacement therapy is considered effective for this disorder (Garfinkel et al.: Lancet, 346, p. 541, 1995). Of aged persons with decreased physiological section of melatonin, those who can sleep well have a large amount of melatonin secreted (Haimov et al.: Sleep. 18, p. 598, 1995). Based on these facts, endogenous melatonin is regarded as a physiological hypnotic substance which takes part in the regulation of the sleep-wakefulness rhythm.

Concerning the hypnotic action of exogenous melatonin, varieties of results have been reported. A report says that the administration of melatonin resulted in upgrading of sleep, such as shortening of hypnagogic latency, decrease in halfway waking, or improvement of insomnia (Zhdanova et al.: Clin. Pharmacol. Ther., 57, p. 552, 1995). On the other hand, there is a report which denies the sleep regulating effect or the sleep disorder improving effect of melatonin (James et al.: Neuropsychopharmacology, 3, p. 19, 1990).

As one of the reasons why these contradictory results were obtained, dosing time dependency has been indicated (Mishima: The Japanese Journal of Clinical Medicine, Vol. 56, No. 2, p. 302, 1998). Another reason may be the fact that melatonin is easily oxidized. In vivo melatonin is known to be metabolized and deactivated by the oxidative ring cleavage reaction of the indole ring by indoleamine-2,3-dioxygenase in the presence of superoxide anions (Hayaishi: J. Biochem., 79, p. 13, 1976). Thus, this reaction easily proceeds in aged persons in whom, or under stress under which, an active oxygen or radical concentration, a cause for occurrence of superoxide anions, is said to be high. Eventually, the concentration of melatonin may lower, making regulation of sleep difficult.

As discussed above, melatonin is clearly a factor involved in the regulation of the circadian rhythm, but much remains to be solved for the full performance of its therapeutic effect. Accordingly, if a circadian rhythm normalizing action can be found in other naturally occurring compounds, their value is very high for use in the prevention of sleep disorder and its associated various diseases. If a compound capable of raising the bioavailability of endogenous melatonin and exogenous melatonin safely and effectively is obtained from a natural substance, its value in use is extremely high.

Astaxanthin is a red carotenoid pigment seen in aquatic animals such as crustaceans or fish, and microorganisms. Astaxanthin has been used as a body color improver for fish, or as an additive for improvement of the color tone of domestic animals (Japanese Unexamined Patent Publication No. 206342/82, Japanese Unexamined Patent Publication No. 54647/85, and Japanese Unexamined Patent Publication No. 63552/92). The antioxidant action of astaxanthin has been demonstrated to be more potent than that of $\alpha$-tocopherol, so that astaxanthin is expected to find use as an anti-oxidizing agent, a health food, a cosmetic, and a drug, in addition to application as a natural pigment (Eiji Yamashita: Foods and Development, vol. 27, No. 3, p. 38, 1992). Recently, it has been reported that astaxanthin, administered at a dose $1/100$ the dose of $\alpha$-tocopherol, can suppress increases in lipid peroxides in the brain caused by irradiation with $^{60}Co$ (Nishigaki et al.: J. Clin. Biochem. Nutr., 16, p. 161, 1994).

However, it has not been known that astaxanthin has the action of normalizing the circadian rhythm, and is effective for preventing or alleviating sleep disorder and various diseases due to disturbance of the circadian rhythm. Nor is astaxanthin known to enhance the circadian rhythm regulating action of melatonin. Furthermore, it has not been known thus far to use astaxanthin as a food or beverage, a food additive, or an active ingredient of a drug, intended for a circadian rhythm normalizing effect and a hypnotic action.

DISCLOSURE OF THE INVENTION

An object to be attained by the present invention is to provide a composition, which is highly safe, which regulates the circadian rhythm effectively, and which is aimed at preventing or alleviating medical symptoms of sleep disorder and various diseases due to disturbance of the circadian rhythm, and a food, beverage or drug containing the composition.

Another object of the invention is to provide a composition, which acts to increase the availability of melatonin in vivo, effectively regulating the circadian rhythm, and a food, beverage or drug containing the composition.

To search for a substance having the action of normalizing the circadian rhythm, the inventors of the present invention conducted studies on various substances with the use of a circadian rhythm measuring method, with the amount of spontaneous movement of rats as an indicator, in an environment controlled to have a 12-hour light period and a 12-hour dark period. As a result, the inventors have clarified that astaxanthin, which is one of carotenoids, and/or its ester has a circadian rhythm normalizing action. Further, they have found that the circadian rhythm normalizing action of melatonin can be enhanced by ingesting astaxanthin and/or its ester and melatonin in combination. These findings led them to accomplish the present invention.

The present invention provides a composition, such as a drug or a food, which contains astaxanthin and/or its ester as an active ingredient, or which contains melatonin, astaxanthin and/or its ester so as to be ingestible in combination. Such a combination is highly safe, and shows a circadian rhythm normalizing action.

EMBODIMENTS OF THE INVENTION

The present invention made it possible to search for a substance having a circadian rhythm normalizing action with the use of a circadian rhythm measuring method, with the amount of spontaneous movements of rats reared in a controlled environment being used as an indicator. As a result, astaxanthin, which is one of carotenoids, and/or its ester has been found to have a circadian rhythm normalizing action. That is, by taking astaxanthin into rats with a disturbed circadian rhythm, the circadian rhythm of the rats was successfully brought close to the normal value.

Further, the present invention has found that the circadian rhythm normalizing action of melatonin can be enhanced by ingesting astaxanthin and/or its ester and melatonin simultaneously. This enhancive action was not observed in $\alpha$-tocopherol, an antioxidant like astaxanthin. This action of astaxanthin has been attributed to the antioxidant action of astaxanthin, because melatonin is a compound susceptible to oxidative decomposition. In other words, the effect of enhancing the circadian rhythm normalizing action of melatonin has been assumed to be an action common to anti-oxidizing substances. Thus. $\alpha$-tocopherol, an antioxidant like astaxanthin, was used instead of astaxanthin to compare the effects of $\alpha$-tocopherol and astaxanthin (Example 3). As a result, 0.001% and 0.005% of $\alpha$-tocopherol showed no effect of enhancing the circadian rhythm normalizing action of melatonin. On the other hand, 0.0045% of astaxanthin was found to enhance the circadian rhythm normalizing action of melatonin significantly. This has not been known as the action of astaxanthin.

The astaxanthin and/or its ester of the present invention can take various forms, and can be supplied as foods, such as common foods, health foods, functional foods, and nutrient supplement foods, or drugs. The amount of melatonin used when melatonin is jointly used may be suitably increased or decreased according to the amount necessary to exhibit the function of melatonin. In the composition of the present invention, its dose may be as low as 50 to 80% of the dose so far required, since the availability of melatonin in vivo is improved in the composition.

The astaxanthin and/or its ester, the active ingredient of the present invention, has been discovered from the crust and egg of crustaceans (Kuhn et al.: Angew. Chem., 51, p. 465, 1938 or Ber., 71, p. 1879, 1938), organs (Kuhn et al.: Ber. 72, p. 1879, 1939), plants (Tischer et al.: Z. Physiol. Chem., 267, p. 281, 1941), petals of Amur Adonis or buttercup (Seybold et al.: Nature, 184, p. 1714, 1959), skin of various fishes and shellfishes (Matsuno et al.: Carotenoids Chemistry and Biology, Plenum Press, p. 59, 1989), egg (Miki et al.: Comp. Biochem. Physiol., 71B, p.7, 1982), Antarctic krills (Yamaguchi et al.: Bull. Japan. Soc. Sci. Fish, 49, p. 1411, 1983), Haematococcus of Chlorophyceae (Renstroem et al.: Phytochem. 20, p. 2561, 1981), red yeast Phaffia (Andrewes et al.: Phytochem., 15, p. 1003, 1976), and marine bacterium Agrobacterium aurantiacum (Yokoyama et al.: Biosci. Biotech. Biochem., 58, p. 1842, 1994). The chemical structure of astaxanthin has been determined (Andrewes et al.: Acta Chem. Scand., B28, p. 730, 1974), and a method for its organic synthesis has also been established (Widmer et al.: Helv. Chem. Acta., 64, p. 2405, 1981, Mayer et al.: Helv. Chem. Acta., 64, p. 2419, 1981). Thus, astaxanthin can be easily obtained as a chemical synthetic product.

The active ingredient in the present invention may be chemically synthesized astaxanthin, or may be an extract from the crust of crustaceans such as red yeast, Tigriopus (red water flea) or krills, or green algae, or minute algae (may be in the state of a solvent extract, or if desired, a suitably purified material) which contains astaxanthin and/or its ester. Alternatively, there can be used a powder formed by pulverizing crustaceans or green algae of the genus Haematococcus containing astaxanthin and/or its ester.

For example, the following are cited as methods for preparation of astaxanthin and/or its ester: methods for preparation utilizing crustaceans (Japanese Unexamined Patent Publication Nos. 1983-88353 and 1989-186860), methods for preparation utilizing algae (Japanese Unexamined Patent Publication No. 1989-187082, Officially Published Patent Gazette No. 1990-501189, Japanese Unexamined Patent Publication No. 1993-68585, Japanese Unexamined Patent Publication No. 1991-83577), methods for preparation utilizing astaxanthin-producing yeast (Officially Published Patent Gazette No. 1990-504101, Japanese Unexamined Patent Publication No. 1991-206880, Japanese Unexamined Patent Publication No. 1992-228064), and methods for preparation utilizing krills (Japanese Unexamined Patent Publication No. 1985-4558, Japanese Unexamined Patent Publication No. 1986-281159, Eiji Yamashita: Foods and Development, vol. 27, p. 38(1992)). Novel synthesis of astaxanthin (Japanese Unexamined Patent Publication No. 1992-225933) is also disclosed. Other methods can be used alone or in combination, if they enable the properties of the active ingredient of the present invention to be effectively utilized.

The ester of astaxanthin used in the present invention is an ester of astaxanthin with an arbitrary fatty acid acceptable for foods or medicines. Examples of the fatty acid are saturated fatty acids, such as palmitic acid and stearic acid, or unsaturated fatty acids such as oleic acid, linoleic acid, α-linolenic acid, γ-linolenic acid, bishomo-γ-linolenic acid, arachidonic acid, eicosapentaenoic acid, and docosahexaenoic acid. Any monoesters or diesters comprising one or two of them joined to astaxanthin can be used in the present invention.

When the active ingredient of the present invention is used as a food or drug, any of the above-described crude extracts or purified products can be used. When any of them is used, the active ingredient can be emulsified according to the customary method, or can be emulsified with the addition of a compound which will be a synergist, because astaxanthin and its ester are oily.

Astaxanthin and/or its ester, the active ingredient of the food, beverage or drug of the present invention, is contained in such an effective amount, for example, of 0.5 to 500 mg/day, preferably 5 to 50 mg/day, as will exhibit a circadian rhythm normalizing action when the food, beverage or drug is taken into the body. However, there is no restriction on the upper limit of the active ingredient.

Melatonin in the present invention, on the other hand, may be a synthetic product, or may be an extract from an animal or plant containing melatonin, or a purified product or a crude extract. Any of them can be used without any restriction.

Astaxanthin and/or its ester can be added to or combined with melatonin in a varying ratio, and ingested. To exhibit the effect of the present invention, the amount of astaxanthin and/or its ester is desirably 3 to 6 times the weight of melatonin.

For the composition or preparation of the food, beverage or drug of the present invention, astaxanthin and/or its ester as the active ingredient of the present invention may be a chemically synthesized product, or a naturally occurring substance. They can be used singly or in a suitable combination. Astaxanthin or the crude extract can be dissolved in ethanol, and used as such or after dilution with water.

If desired, an emulsified preparation can be produced. To produce the emulsified preparation, gallic acid, L-ascorbic acid (or its ester or salt), gum (such as locust bean gum, gum Arabic, or gelatin), and further vitamin P (e.g., flavonoids or polyphenols such as hesperidin, rutin, quercetin, catechin, and cyanidin, or mixtures thereof) can be added to the aqueous phase. To the oil phase, astaxanthin or its ester, the crude extract, or a mixture thereof can be added. Further, glycerol, glycerin fatty acid ester, sorbitan fatty acid ester, sucrose fatty acid ester, dextrin, or oils and fats, such as ordinary liquid oils, e.g., rapeseed oil, soybean oil, or corn oil, can be added. These materials are emulsified, whereby the emulsified preparation can be easily prepared. For emulsification, a high speed agitator, a homogenizer or the like can be used to perform emulsification with mixing.

The active ingredient as the drug of the present invention is orally administered as a solid dosage form such as tablets or powder, or a liquid dosage form such as an elixir, a syrup or a suspension. Parenterally, the drug can be used, for example, as an injection or suppositories. Adjuvants for use in the oral drug include, for example, carriers in the form of solid powders, sugars such as lactose and saccharose, amino acids such as glycine, and cellulose. As lubricants, silicon dioxide, talc, magnesium stearate, and polyethylene glycol can be exemplified. As binders, starch, gelatin, methyl cellulose, and polyvinyl pyrrolidone can be cited. Disintegrants include starch and agar.

The composition of the present invention has the action of normalizing the circadian rhythm, and so can be used for the purpose of prevention or alleviation of circadian rhythmical sleep disorder. The composition can also be used for normalizing not only the rhythm of sleep, but also the rhythms of hormone secretion, nervous activity, enzyme activity, metabolism, body temperature, renal function, etc. which involve circadian rhythms. Hence, the composition can prevent or alleviate medical symptoms of various diseases associated with the abnormality of these rhythms. Alleviation or improvement of the symptoms in the present invention include the treatment of diseases.

Moreover, the astaxanthin of the present invention has the effect of enhancing the circadian rhythm normalizing action of melatonin. Surprisingly, this action was not noted in the same dose of α-tocopherol, an antioxidant. Hence, the mere fact that astaxanthin is an antioxidant cannot explain the action and effect of astaxanthin that enhances the circadian rhythm normalizing action of melatonin.

The amount of astaxanthin or its ester (active ingredient) contained in the drug of the present invention is such an amount as can be orally or parenterally administered in a dose of normally 0.5 to 500 mg, preferably 5 to 50 mg, daily in an adult. The dose clearly differs according to the type of disease for which the astaxanthin or its ester is administered, the age of the patient, the body weight of the patient, the severity of symptoms, or the dosage form. The active ingredient of the present invention has a circadian rhythm normalizing action, and thus can prevent or improve sleep disorder and various diseases, such as cardiovascular disorders, which result from the disturbance of the circadian rhythm.

The food or beverage of the present invention can be supplied in the form of common foods, including margarine, butter, butter sauce, cheese (natural cheese, processed cheese), fresh cream, shortening, lard, ice cream, yogurt, coffee milk, dairy products, sauce, soup, meat products, fish products, popcorn, fried potatoes, potato chips, seasoned finely divided foods (e.g., sesame, seaweed, fish meat, egg, and egg) for sprinkling over rice, rolled omelet sometimes containing fish meat paste, Japanese confectionery (rice cracker, etc.), Western confectionery (custard pudding, jelly, gummy candy, candy, drop, caramel, chocolate, chewing gum, pastry, etc.), baked confectionery (sponge cake, cakes, doughnut, biscuit, cookie, cracker, etc.), macaroni, pasta, salad oil, instant soup, dressing, egg, mayonnaise, miso, non-alcoholic beverages such as carbonated beverages, non-carbonated beverages (fruit juice drink, nectar, etc.), soft drinks, sport drinks, tea, coffee, and cocoa, and alcoholic beverages such as liqueur and medicated liquor.

The food or beverage of the present invention can be produced by blending astaxanthin and/or its ester or a product, which has been obtained from a natural substance containing astaxanthin and/or its ester, with raw materials for an ordinary food, and processing the mixture by an ordinary method. The concentration of astaxanthin and/or its ester blended differs according to the dosage form or the shape or properties of the food. Generally, the concentration is preferably, but not restricted to, 0.001 to 10%. However, the food or beverage is prepared such that the active ingredient of the present invention, as astaxanthin, is contained in the necessary amount, per daily intake of the final product, to show a circadian rhythm normalizing action. As far as is known currently, the preferred amount is 0.5 to 500 mg, preferably 5 to 50 mg, per daily intake of the product in the adult. Such an amount can be selected, as desired, by people skilled in the art.

When the food or beverage of the present invention is used as a nutrient supplement food or a functional food, its form may be the same form as the aforementioned pharmaceutical preparation. However, the food or beverage may be in a processed form, such as a liquid natural food, a partially digested nutritional diet, an elemental diet, an ampuled liquid medicine type product, capsules, or an enteral nutrition, which contains, for example, protein (protein of a high nutritional value and having a good amino acid balance, such as milk protein, soybean protein, or ovalbumin, is used most widely as the source of protein, but the decomposition product thereof, the oligopeptide of egg white, the hydrolysis product of soybean, or a mixture of them with a single amino acid is also used), sugars, fat, trace elements, vitamins, emulsifier, and flavors. When the food or beverage is supplied as a sport drink or a nutritional drink, easily digestible carbohydrates, nutritional additives such as amino acids, vitamins and minerals, sweeteners, spices, flavors, and pigments can be incorporated in order to recover the nutritional balance and better the flavor of the food or beverage when ingested.

The nutrient supplement food or functional food of the present invention is not restricted to them, and may be in the form of ordinary foods as described above. If possible, however, it should desirably be in a unit intake form.

The Examples and Referential Examples will be described in detail below, but the present invention is not limited thereby.

EXAMPLE 1

Circadian Rhythm Normalizing Action of Astaxanthin

The influence of astaxanthin on daily movements was investigated in rats. Rats have the habit of resting (sleeping) mainly in the light period, and acting in the dark period. The circadian rhythm of rats was investigated by measuring the amount of daily movements continuously, and examining changes over time in the amounts of movements in the light period and the dark period.

Four-week-old male Wistar rats (purchased from Nippon Charlesriver) were preliminarily reared for one week, and subjected to experiments at the age of 5 weeks. The rats were randomly divided into two groups (5 to 6 rats/group), and one of the groups was used as a control diet (low tocopherol) group, while the other group was used as an astaxanthin diet group, each group receiving the designated diet for 4 weeks. The animals were reared in animal cages kept at room temperature of $23.5 \pm 1°$ C. and a humidity of $55 \pm 5\%$, and the feed and water were provided ad libitum.

Methods for Measuring the Amount of Daily Movements in Rats

Formulation of Feed

The feed was prepared according to the formulation shown in Table 1. Astaxanthin used was astaxanthin extracted from krills and then purified (an oil containing 15% of astaxanthin as a free compound; a product of Itano Refrigerating Co.).

Measurement of the Amount of Rat Daily Movements

The rats were individually reared in a box equipped with an infrared sensor, and the amount of movements was counted with the infrared sensor. That is, each time the animal passed the infrared sensor, the passage was taken as one count. The counts taken were accumulated, and expressed as the amount of movements (counts). Statistical treatment was performed using ANOVA and student t-test.

Figure 1:
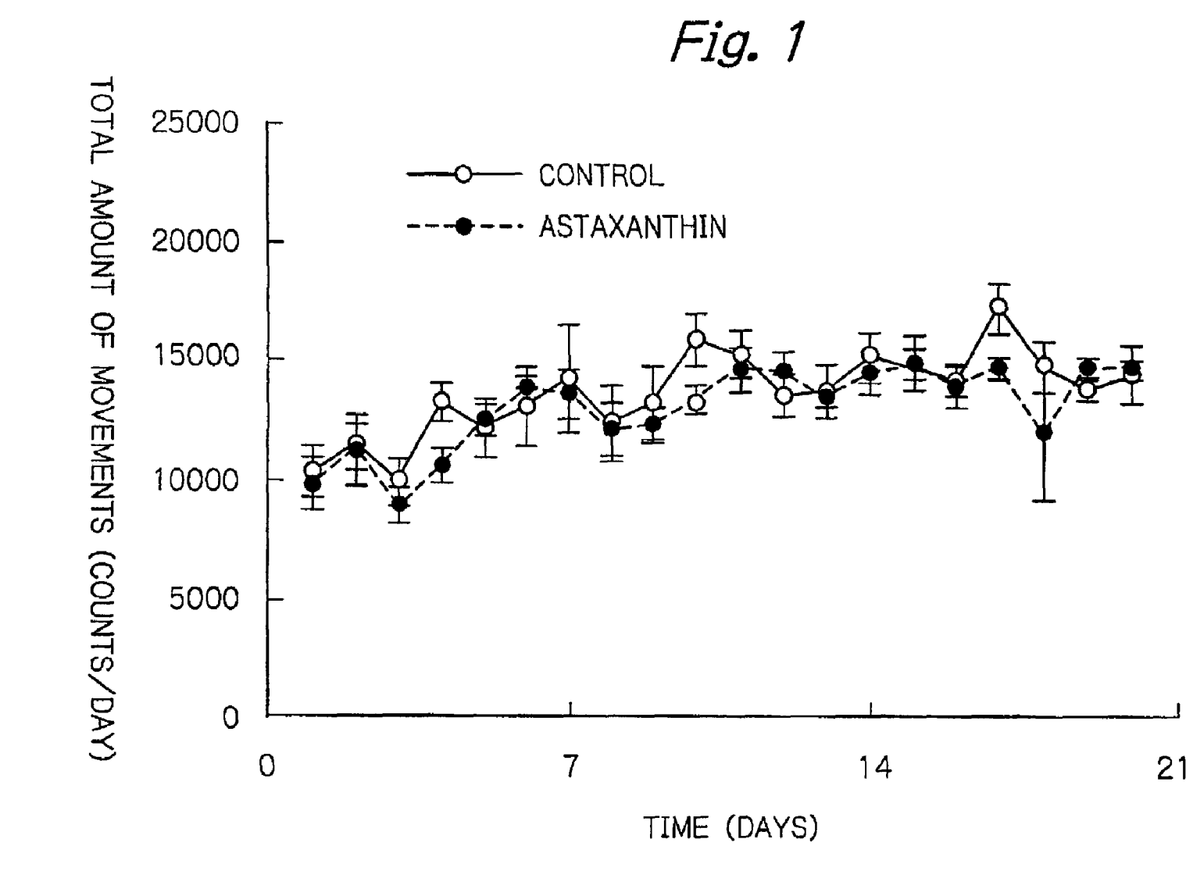
FIG. 1 is a view showing the influence of astaxanthin on the total amount of movements (day-to-day changes).
Figure 2:
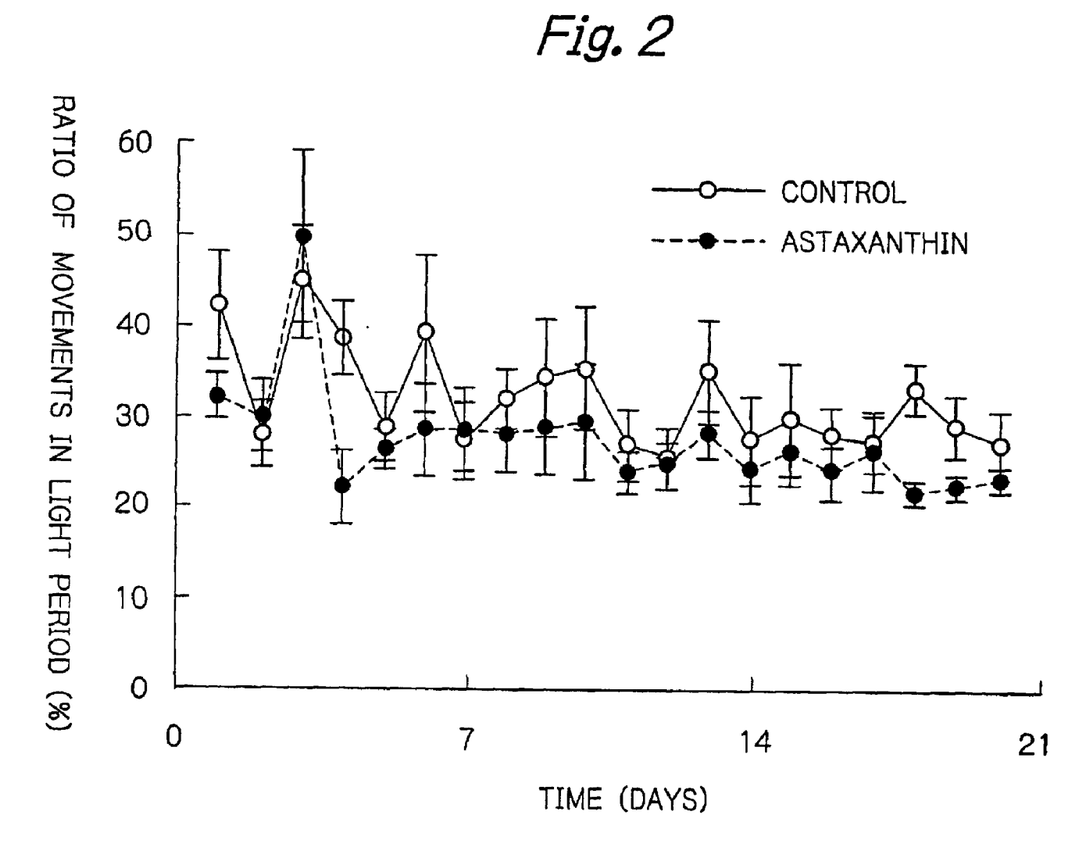
FIG. 2 is a view showing the influence of astaxanthin on the ratio of movements in the light period to the total amount of movements (day-to-day changes).
Figure 3:
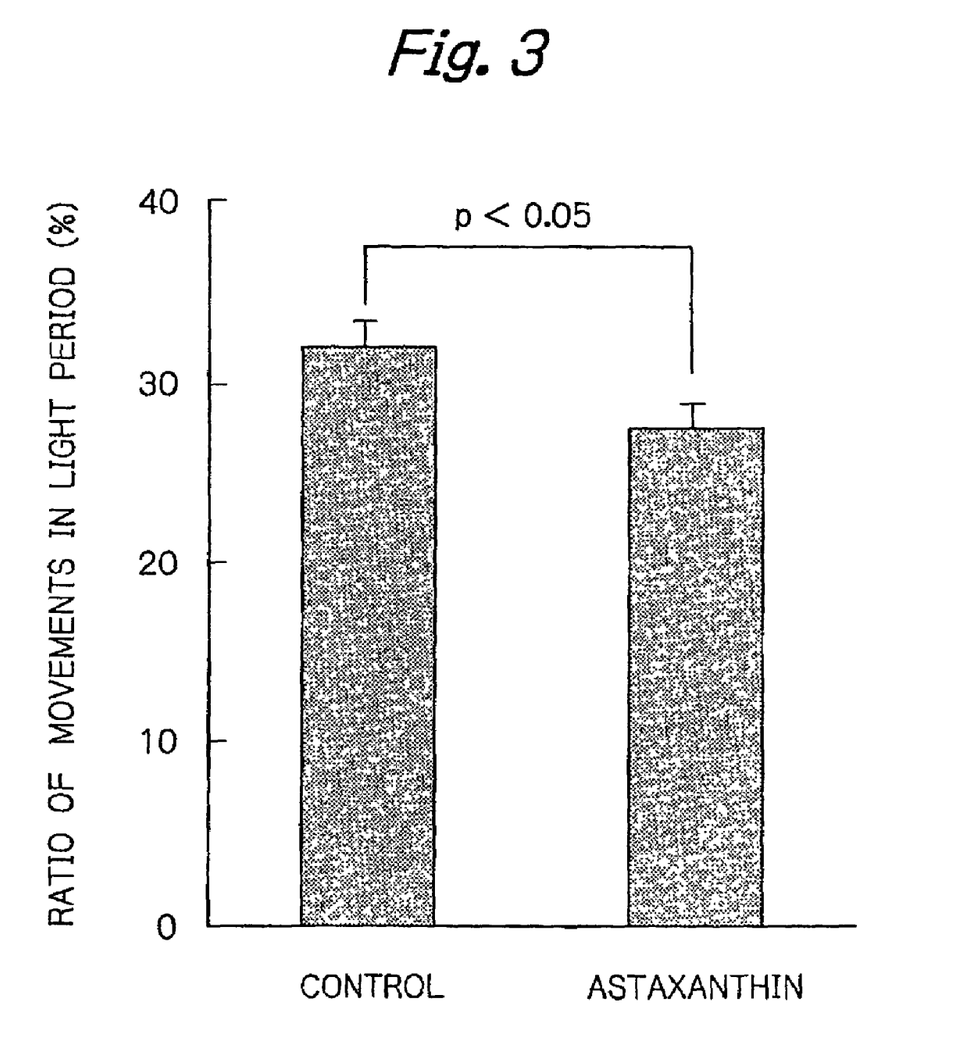
FIG. 3 is a view showing the influence of astaxanthin on the ratio of movements in the light period to the total amount of movements (average).

A period of 1 week after start of rearing with the experimental diet was set as a tuning period in which the animal was tuned to a 12-hour dark period and a 12-hour light period. Then, from the 2nd week, the amount of daily movements was continuously measured for 3 weeks. The total amount of movements, and the ratio of movements in the light period to the total amount of movements (i.e., the amount of movements in the light period/the total amount of movements$\times 100$ (%)) were calculated every day. Astaxanthin did not affect the total amount of movements in comparison with the control (FIG. 1), but lowered the ratio of movements in the light period (FIG. 2). Based on these findings, the ingestion of astaxanthin was found to decrease the activity of rats in the light period, and astaxanthin was confirmed to have the action of stabilizing the circadian rhythm. The averages of the ratio (%) of movements in the light period were compared in both groups (FIG. 3). A significant decrease in the ratio of movements in the light period was observed in the astaxanthin diet group, demonstrating astaxanthin to have the action of normalizing the circadian rhythm.

EXAMPLE 2

Enhancive Effect of Astaxanthin on Circadian Rhythm Normalization by Melatonin

Four-week-old male Wistar rats (purchased from Nippon Charlesriver) were preliminarily reared for one week, and subjected to experiments at the age of 5 weeks. The rats were randomly divided into two groups (10 to 11 rats/group), and the two groups were given a control diet (low tocopherol diet) and an astaxanthin diet (Table 1), respectively. Each group was further divided into two groups (5 to 6 rats/group), which received distilled water and melatonin water, respectively, for 4 weeks. The animals were reared in animal cages kept at room temperature of 23.5±1° C. and a humidity of 55±5%, and the feed and water were provided ad libitum. Melatonin was dissolved in water at a concentration of 0.5 mg/100 ml, and the solution was given ad lib, as drinking water. The intake of melatonin, calculated from the amount of water taken by rats, was about 1 mg/day.

Figure 4:
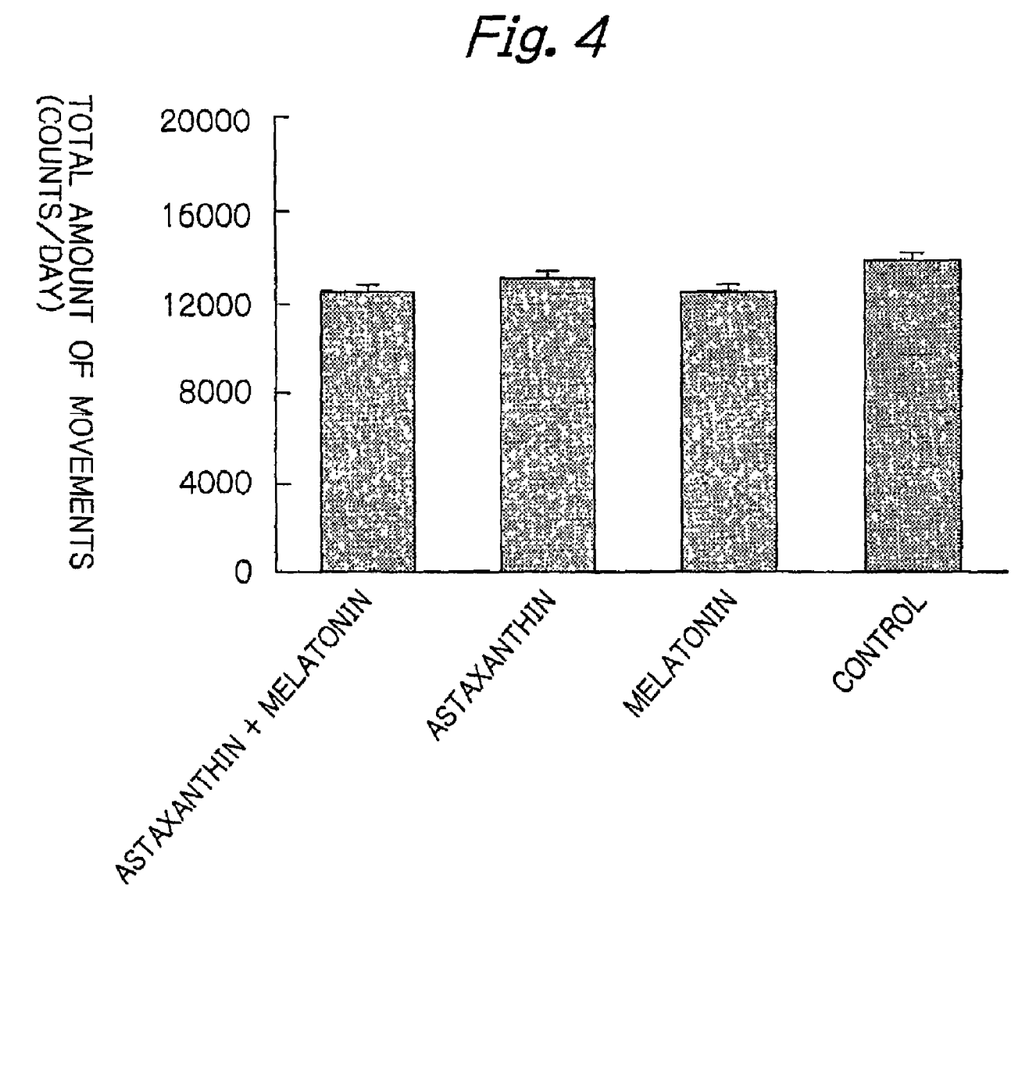
FIG. 4 is a view showing the influences of astaxanthin and melatonin on the total amount of movements (averages).
Figure 5:
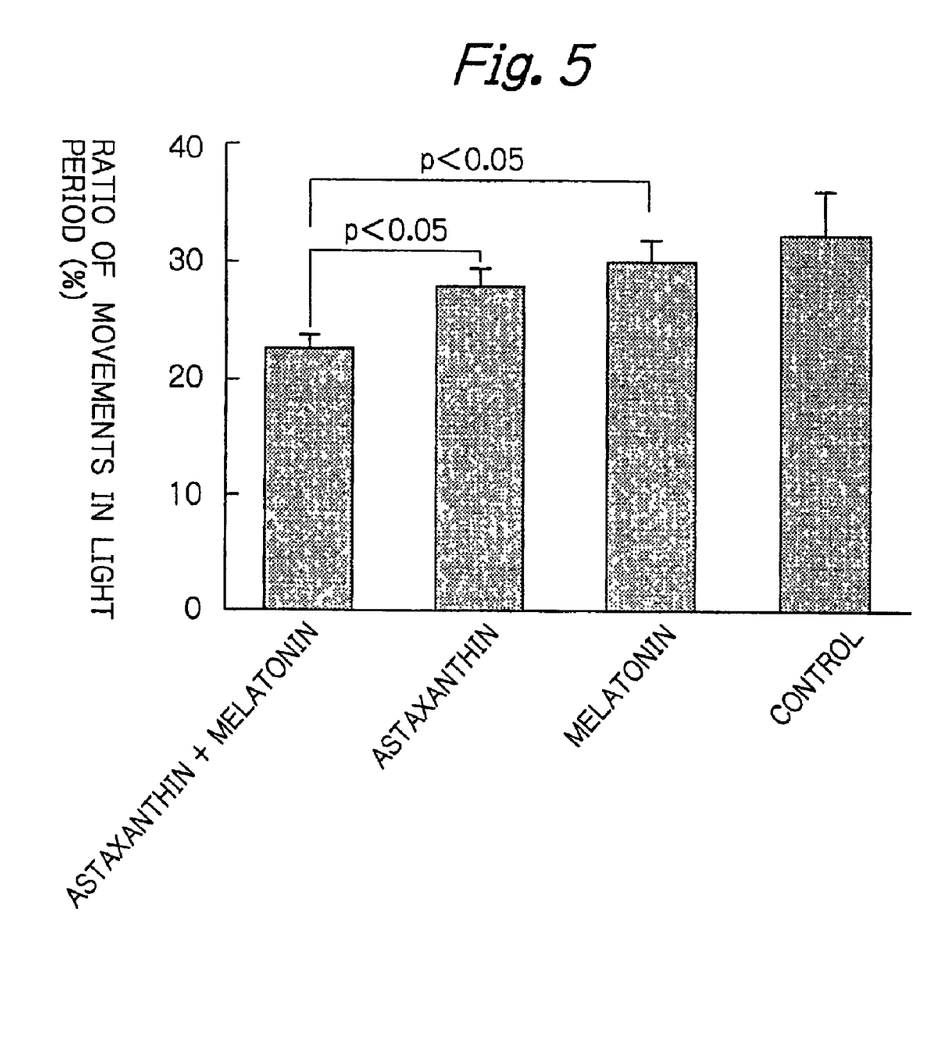
FIG. 5 is a view showing the influences of astaxanthin and melatonin on the ratio of movements in the light period (averages).

After start of rearing with the experimental diet, a tuning period of 1 week was provided. Then, the amount of movements of rats was measured as in Example 1 for 3 weeks to look into changes in the circadian rhythm. No differences were noted among the averages of the total amount of movements in the respective groups (FIG. 4). The ratio of activity in the light period to the total amount of movements (the amount of movements in the light period/the total amount of movements×100 (%)) was compared in the respective groups. A tendency toward a decrease in the ratio of activity in the light period was seen even in the astaxanthin group or melatonin group alone as compared with the control group. Astaxanthin and melatonin administered simultaneously further enhanced the circadian rhythm normalizing action (FIG. 5).

EXAMPLE 3

Comparison with the Enhancive Effect of α-Tocopherol on Circadian Rhythm Normalization by Melatonin The influence that α-tocopherol, a liposoluble antioxidant like astaxanthin, exerts on the circadian rhythm normalizing action of melatonin was compared with that of astaxanthin.

Four-week-old male Wistar rats (purchased from Nippon Charlesriver) were preliminarily reared for one week, and subjected to experiments at the age of 5 weeks. The rats were randomly divided into two groups (10 to 11 rats/group), and each group was given 0.001% and 0.005% tocopherol diets. Each group was further divided into two groups (5 to 6 rats/group), and one of the groups received distilled water for 4 weeks, while the other group received melatonin water for 4 weeks. The animals were reared in animal cages kept at room temperature of 23.5±1° C. and a humidity of 55±5%, and the feed and water were provided ad libitum.

Figure 6:
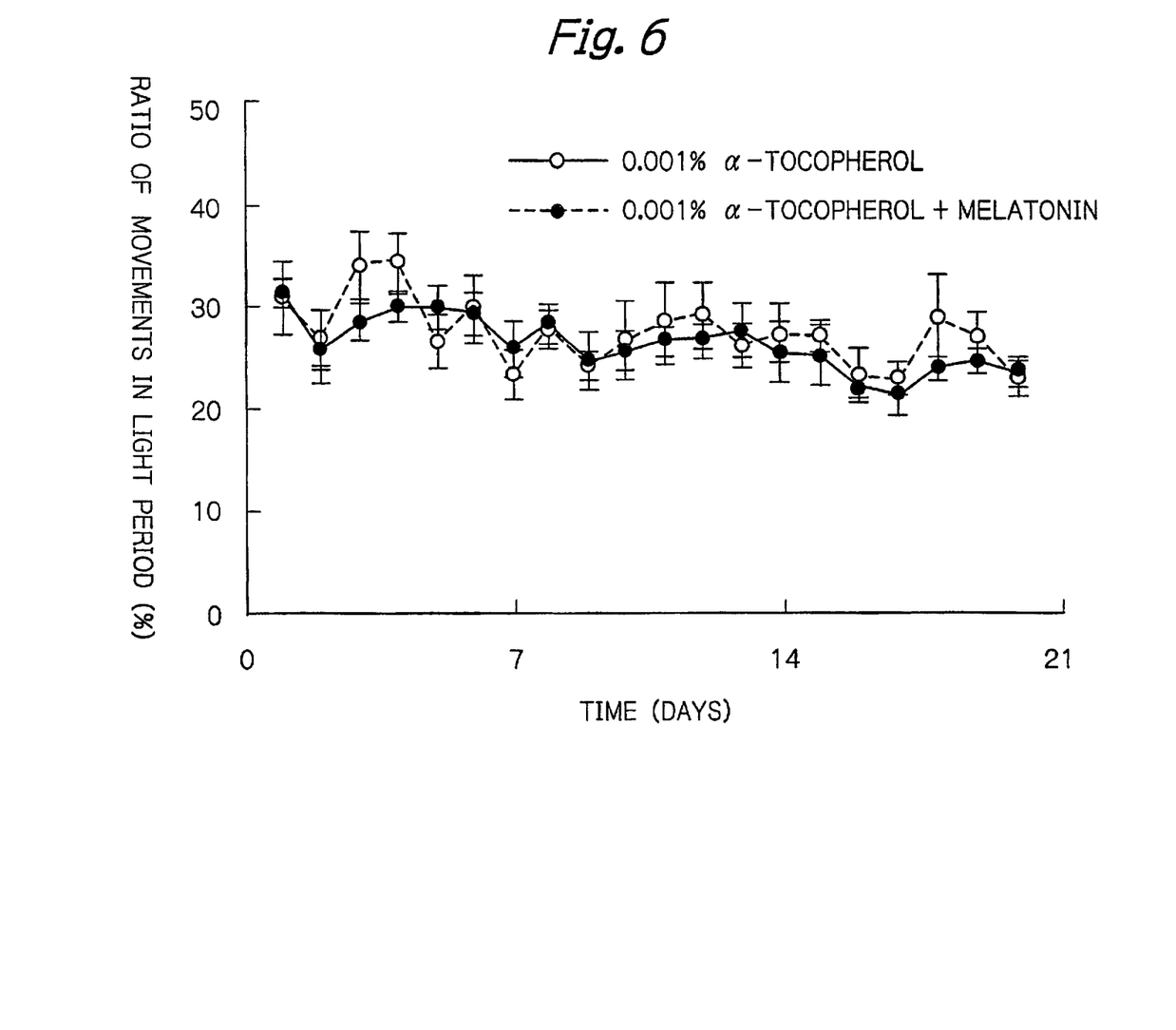
FIG. 6 is a view showing the effect of low-dose $\alpha$-tocopherol on the circadian rhythm normalizing action of melatonin.
Figure 7:
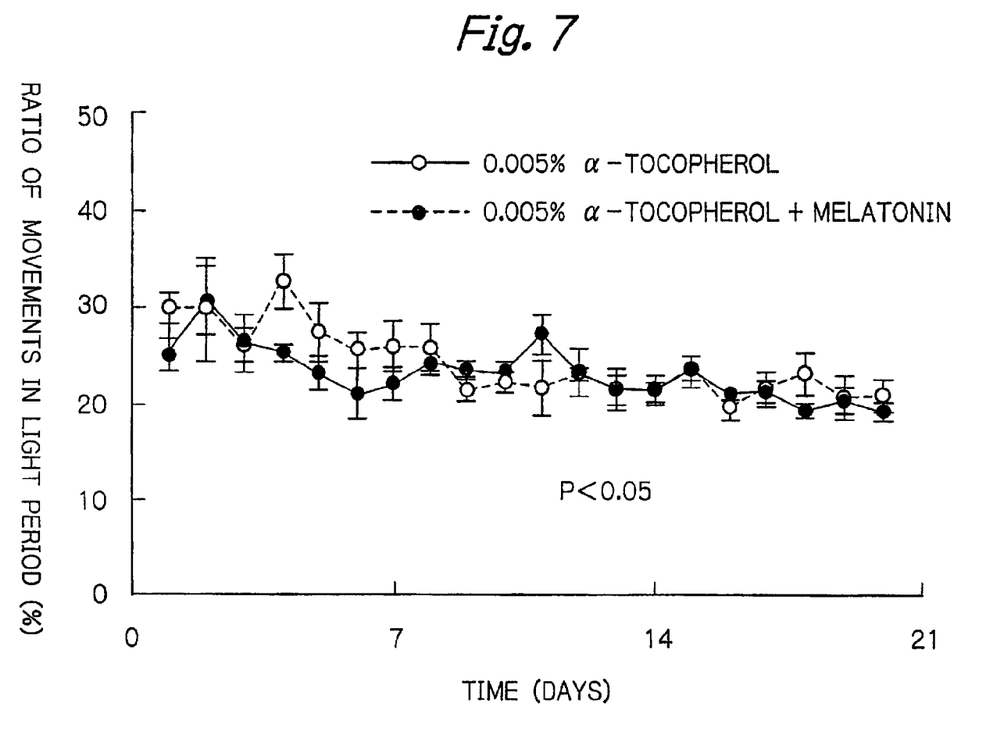
FIG. 7 is a view showing the effect of high-dose $\alpha$-tocopherol on the circadian rhythm normalizing action of melatonin.
Figure 8:
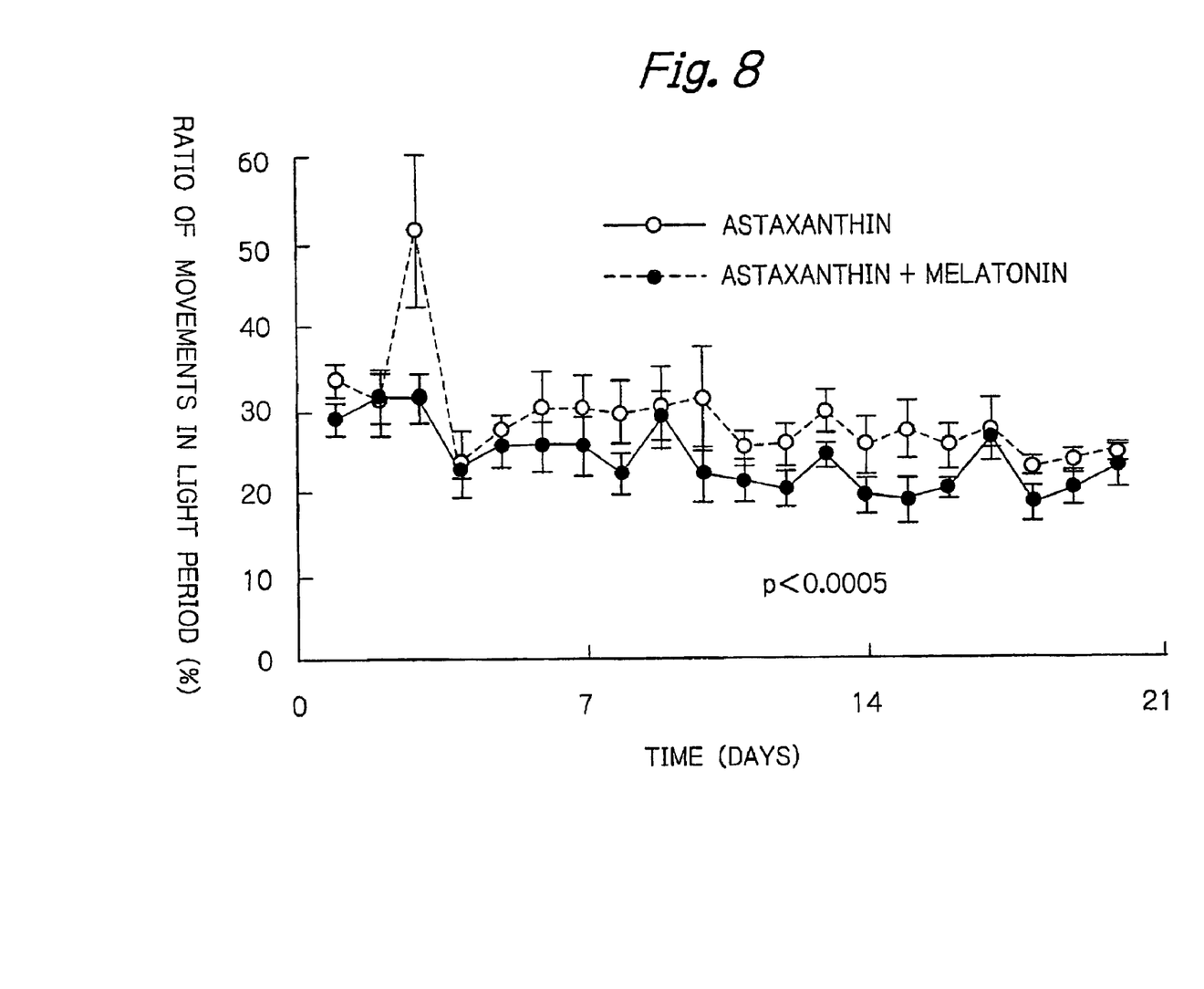
FIG. 8 is a view showing the effect of astaxanthin on the circadian rhythm normalizing action of melatonin.

After start of rearing with the experimental diet, a tuning period of 1 week was provided. Then, the amount of movements of rats was measured for 3 weeks in the same manner as in Example 1 to look into changes in the circadian rhythm. Day-to-day changes in the ratio of movements in the light period to the total amount of movements (i.e., the amount of movements in the light period/the total amount of movements×100 (%)) are shown in FIGS. 6, 7 and 8. An enhancive effect on the circadian rhythm normalizing action of melatonin was not observed in the 0.001% tocopherol diet group (FIG. 6). A slight enhancive effect on the circadian rhythm normalizing action of melatonin was observed in the 0.005% tocopherol diet group (FIG. 7). However, the enhancive effect on the circadian rhythm normalizing action of melatonin, which was observed in the 0.005% tocopherol diet group, was weaker than the enhancive effect on the circadian rhythm normalizing action of melatonin that was observed in the 0.0045% astaxanthin diet group (FIG. 8). These results clarify that astaxanthin has a more potent effect of enhancing the circadian rhythm normalizing action of melatonin than does α-tocopherol.

EXAMPLE 4

Dose Dependency of the Circadian Rhythm Normalizing Action of Astaxanthin

Four-week-old male Wistar rats (purchased from Nippon Charlesriver Co.) were preliminarily reared for one week, and subjected to experiments at the age of 5 weeks. The rats were randomly divided into five groups, which were given a control diet (tocopherol-deficient diet) and astaxanthin diets (Table 2), respectively. The feed and water were provided ad libitum. The amount of astaxanthin intake calculated from the amount of the feed taken into the rats was about 2 to 20 mg/day.

Figure 9:
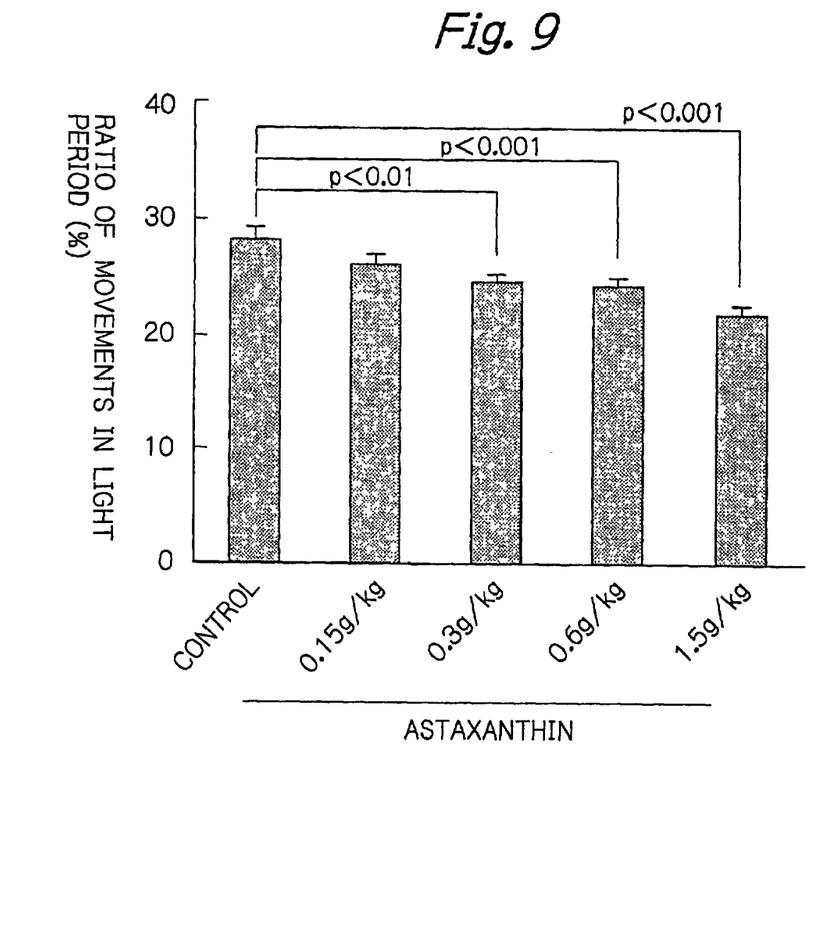
FIG. 9 is a view showing the effect (dose dependency) of astaxanthin on the ratio of movements in the light period (averages).
Figure 10:
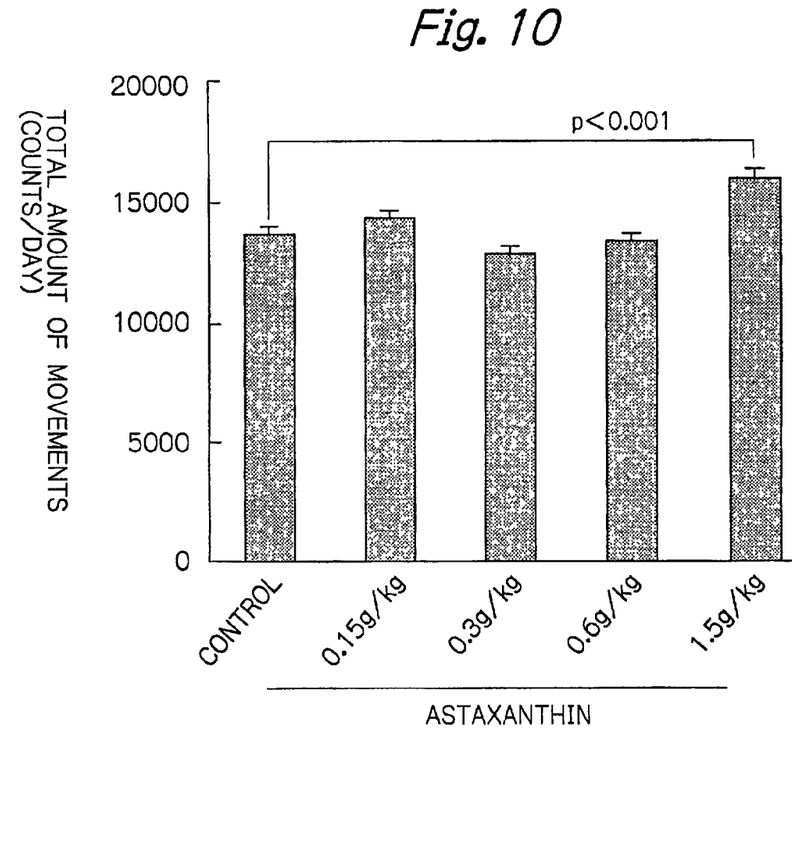
FIG. 10 is a view showing the effect (dose dependency) of astaxanthin on the total amount of movements (averages).

After a tuning period of 1 week, the amount of movements of rats was measured for 3 weeks in the same manner as in Example 1 to investigate changes in the circadian rhythm. The ratio of activity in the light period to the total amount of movements (i.e., the amount of movements in the light period/the total amount of movements×100 (%)) decreased in an astaxanthin concentration-dependent manner, starting with a minimum dose of 0.15 g/kg diet. The decrease was significant at doses of 0.3 g/kg diet and more (FIG. 9). The total amount of movements, on the other hand, tended to increase at a maximum dose of 1.5 g/kg diet (FIG. 10).

The present example used the tocopherol-deficient diet as the basic feed. As in the case of Example 1, in which the low tocopherol diet was used as the basic feed, the circadian rhythm normalizing action of astaxanthin was confirmed in the present example. Thus, astaxanthin was confirmed to act effectively even when tocopherol was deficient to disturb the circadian rhythm.

| [Preparation Example 1] Emulsified preparation | |
|---|---|
| | (% by weight) |
| Oil phase | |
| Astaxanthin | 0.1 |
| Rapeseed oil | 39.9 |
| Succinic acid glyceride | 2.0 |
| Aqueous phase | |
| L-Ascorbic acid | 2.0 |
| Gallic acid | 1.0 |
| Quercetin | 1.0 |
| Locust beam gum | 0.1 |
| Water | 53.9 |

Water having locust beam gum dissolved therein was heated to 65° C., and then mixed with gallic acid, L-ascorbic acid and quercetin. The oil phase, which had been formed by mixing and dissolution at 65° C. was mixed with the aqueous phase with stirring. The mixture was passed through a homogenizer for homogenization, and cooled to 10° C. to obtain an emulsified preparation of the above formulation. This emulsified preparation is drunk in an amount of about 1 to 20 ml per dose.

[Preparation Example 2]
Emulsified preparation

| | (% by weight) |
|---|---|
| Oil phase | |
| Astaxanthin | 0.1 |
| Rapeseed oil | 38.9 |
| Citric acid monoglyceride | 2.0 |
| Aqueous phase | |
| L-Ascorbic acid | 2.0 |
| Gallic acid | 1.0 |
| Hesperidin | 1.0 |
| Locust beam gum | 0.05 |
| Water | 54.95 |

Water having locust beam gum dissolved therein was heated to 65° C., and then mixed with gallic acid, L-ascorbic acid and hesperidin. The oil phase, which had been formed by mixing and dissolution at 65° C., was mixed with the aqueous phase with stirring. The mixture was passed through a homogenizer for homogenization, and cooled to 10° C. to obtain an emulsified preparation of the above formulation. This emulsified preparation is drunk in an amount of about 1 to 20 ml per dose.

[Preparation Example 3]
Tablets

| | (% by weight) |
|---|---|
| Astaxanthin | 5 |
| Lactose | 80 |
| Heavy magnesium oxide | 15 |

The above materials were mixed uniformly, and formed into tablets with a content of 180 mg/tablet.

[Preparation Example 4]
Powder and granules

| | (% by weight) |
|---|---|
| Astaxanthin | 45 |
| Lactose | 40 |
| Starch | 15 |

The above materials were mixed uniformly, and formed into a powder or granules.

[Preparation Example 5]
Capsules

| | (% by weight) |
|---|---|
| Gelatin | 70.0 |
| Glycerin | 22.9 |

-continued

[Preparation Example 5]
Capsules

| | (% by weight) |
|---|---|
| Methyl para-hydroxybenzoate | 0.15 |
| Propyl para-hydroxybenzoate | 0.51 |
| Water | Proper amount |
| Total | 100% |

Soft capsule shells comprising the above components were charged with a krill extract fat (containing 1.7% astaxanthin diester) by the usual method to obtain soft capsules with a content of 180 mg/capsule.

[Preparation Example 6]
Ampuled liquid medicine

| | | |
|---|---|---|
| Taste: | | |
| Sodium DL-tartrate | 1 | g |
| Succinic acid | 0.09 | g |
| Sweetness: Liquid sugar | 8 | Kg |
| Sourness: Citric acid | 120 | g |
| Vitamins: | | |
| Vitamin C | 100 | g |
| Vitamin E | 300 | g |
| Astaxanthin ethyl ester | 10 | g |
| Cyclodextrin | 50 | g |
| Flavor | 150 | ml |
| Potassium chloride | 10 | g |
| Magnesium sulfate | 5 | g |

The above components were blended, and water was added to make a total amount of 100 liters. The resulting ampuled liquid medicine is drunk in an amount of about 100 ml per dose.

[Preparation Example 7]
Melatonin-containing tablets

| | (% by weight) |
|---|---|
| Astaxanthin | 6 |
| Melatonin | 2 |
| Vitamin $B_6$ | 10 |
| Calcium | 30 |
| Heavy magnesium oxide | 51 |

The above materials were mixed uniformly, and formed into tablets with a content of 100 mg/tablet.

[Preparation Example 8]
Melatonin-containing capsules

| | (% by weight) |
|---|---|
| Gelatin | 70.0 |
| Glycerin | 22.9 |
| Methyl para-hydroxybenzoate | 0.15 |
| Propyl para-hydroxybenzoate | 0.51 |
| Water | Proper amount |
| Total | 100% |

Soft capsule shells comprising the above components were charged with a krill extract fat (5% astaxanthin as a free compound) and melatonin by the usual method to obtain soft capsules with a content of 180 mg/capsule.

[Industrial Applicability]

The astaxanthin and/or its ester, contained in the food, beverage or drug of the present invention, has a circadian rhythm normalizing action as described in the Examples. The protective effect of astaxanthin and/or its ester on endogenous melatonin, or exogenous melatonin ingested simultaneously with astaxanthin, enhances the efficacy of melatonin, acting to normalize the circadian rhythm. In the prior art, no substances having such an action have been known.

TABLE 1

Formulation of Experimental Feed

| Component | Amount (g/kg) | |
| --- | --- | --- |
| | Control diet | Astaxanthin diet |
| Casein (α-tocopherol free) | 200 | 200 |
| DL-methionine | 3 | 3 |
| Corn starch | 150 | 150 |
| Sucrose | 500 | 500 |
| Cellulose powder | 50 | 50 |
| Lard (α-tocopherol free) | 50 | 50 |
| Minerals (AIN-76) | 35 | 35 |
| Vitamins (AIN-76, α-tocopherol free) | 10 | 10 |
| Choline bitartrate | 2 | 2 |
| α-Tocopherol | 0.01 | 0.01 |
| Astaxanthin* | — | 0.3 |

*Oil containing 15% astaxanthin as a free compound

TABLE 2

Formulation of Experimental Feed

| Component | Amount (g/kg) | | | | |
| --- | --- | --- | --- | --- | --- |
| | Control diet | Astaxanthin diet | | | |
| | | 0.15 | 0.3 | 0.6 | 1.5 |
| Casein (α-tocopherol free) | 200 | 200 | 200 | 200 | 200 |
| DL-methionine | 3 | 3 | 3 | 3 | 3 |
| Corn starch | 150 | 150 | 150 | 150 | 150 |
| Sucrose | 500 | 500 | 500 | 500 | 500 |
| Cellulose powder | 50 | 50 | 50 | 50 | 50 |
| Lard (α-tocopherol free) | 50 | 50 | 50 | 50 | 50 |
| Minerals (AIN-76) | 35 | 35 | 35 | 35 | 35 |
| Vitamins (AIN-76, α-tocopherol free) | 10 | 10 | 10 | 10 | 10 |
| Choline bitartrate | 2 | 2 | 2 | 2 | 2 |
| Astaxanthin* | — | 0.15 | 0.3 | 0.6 | 1.5 |

*Oil containing 15% astaxanthin as a free compound

The invention claimed is:

1. A method of normalizing circadian rhythm by administering to a patient suffering from disturbance of circadian rhythm, an effective amount of astaxanthin and/or an ester thereof, and an effective amount of melatonin.

2. The method of claim 1 wherein said effective amount of astaxanthin and/or an ester thereof ranges from 0.5–500 mg/day.

3. The method of claim 1 wherein said effective amount of astaxanthin and/or an ester thereof ranges from 5–50 mg/day.

* * * * *